(12) United States Patent
Heinl et al.

(10) Patent No.: US 7,216,383 B2
(45) Date of Patent: May 15, 2007

(54) SUPPORT DEVICE FOR A PATIENT

(75) Inventors: Dieter Heinl, Erbendorf (DE); Arnulf Oppelt, Spardorf (DE); Markus Petsch, Erlangen (DE); Johann Seissl, Erlangen (DE); Kerstin Waldbach, Porstendorf (DE)

(73) Assignee: Siemens Aktiengesellschaft (DE)

( * ) Notice: Subject to any disclaimer, the term of this patent is extended or adjusted under 35 U.S.C. 154(b) by 112 days.

(21) Appl. No.: 10/929,006

(22) Filed: Aug. 27, 2004

(65) Prior Publication Data

US 2005/0060804 A1    Mar. 24, 2005

Related U.S. Application Data

(60) Provisional application No. 60/499,509, filed on Sep. 2, 2003.

(30) Foreign Application Priority Data

Sep. 1, 2003    (DE) ................. 103 40 552

(51) Int. Cl.
*A61B 6/04* (2006.01)
*A61G 7/08* (2006.01)
(52) U.S. Cl. .............. 5/601; 5/81.1 R; 5/81.1 HS
(58) Field of Classification Search ............ 5/601, 5/621, 630, 632, 625–628, 81.1 R, 81.1 HS, 5/81.1 T; 378/209
See application file for complete search history.

(56) References Cited

U.S. PATENT DOCUMENTS

| | | | | |
|---|---|---|---|---|
| 3,151,343 A | * | 10/1964 | McCormick | 5/627 |
| 3,739,407 A | | 6/1973 | Stiller | 5/81.1 R |
| 3,962,736 A | * | 6/1976 | Fedele | 5/81.1 HS |
| 4,067,079 A | | 1/1978 | Buchman | 5/81.1 R |
| 4,272,856 A | * | 6/1981 | Wegener et al. | 5/81.1 T |
| 4,517,690 A | * | 5/1985 | Wegener | 5/81.1 R |
| 4,528,704 A | * | 7/1985 | Wegener et al. | 5/81.1 R |
| 4,686,719 A | * | 8/1987 | Johnson et al. | 5/81.1 R |
| 4,700,416 A | * | 10/1987 | Johansson | 5/81.1 T |

(Continued)

FOREIGN PATENT DOCUMENTS

DE    197 31 234 A1    2/1999

(Continued)

OTHER PUBLICATIONS

German Office Action dated Nov. 25, 2005 with English Translation.

*Primary Examiner*—Robert G. Santos
(74) *Attorney, Agent, or Firm*—Brinks, Hofer, Gilson & Lione

(57) ABSTRACT

A patient support device which can be connected to patient placement devices of medical examination or treatment equipment, for example an MRI device, an X-ray machine, or of ambulances. The patient support device supports a patient during medical examination and treatment. The patient support device has a structural rigidity that is less than a minimal rigidity that enables the patient support device to be self-supporting while the patient is resting thereon. Such a patient support device can be designed in a simple manner in such a way that it can be used in MRI devices, as well as in devices of other types, and can be transferred between the devices without repositioning of the patient on different support devices.

7 Claims, 3 Drawing Sheets

U.S. PATENT DOCUMENTS

| | | | |
|---|---|---|---|
| 4,793,008 A * | 12/1988 | Johansson | 5/81.1 T |
| 4,805,626 A * | 2/1989 | DiMassimo et al. | 600/415 |
| 4,908,889 A * | 3/1990 | Lonardo | 5/81.1 T |
| 5,065,464 A * | 11/1991 | Blanchard et al. | 5/81.1 R |
| 5,067,189 A * | 11/1991 | Weedling et al. | 5/81.1 R |
| 5,121,514 A * | 6/1992 | Rosane | 5/628 |
| 5,152,016 A * | 10/1992 | Becker | 5/81.1 HS |
| 5,193,233 A * | 3/1993 | Miller | 5/81.1 R |
| 5,271,110 A * | 12/1993 | Newman | 5/81.1 R |
| 5,475,884 A * | 12/1995 | Kirmse et al. | 5/601 |
| 5,493,741 A * | 2/1996 | Baer | 5/86.1 |
| RE35,299 E * | 7/1996 | Weedling et al. | 5/81.1 T |
| 5,561,873 A * | 10/1996 | Weedling | 5/713 |
| RE35,468 E * | 3/1997 | Newman | 5/81.1 R |
| 5,742,958 A * | 4/1998 | Solazzo | 5/81.1 R |
| 5,771,513 A | 6/1998 | Kirchgeorg et al. | 5/625 |
| 5,860,174 A * | 1/1999 | Failor | 5/81.1 HS |
| 6,073,291 A * | 6/2000 | Davis | 5/711 |
| 6,101,644 A * | 8/2000 | Gagneur et al. | 5/81.1 R |
| 6,467,106 B1 * | 10/2002 | Heimbrock | 5/81.1 C |
| 6,640,364 B1 * | 11/2003 | Josephson et al. | 5/601 |
| 6,701,544 B2 * | 3/2004 | Heimbrock | 5/81.1 R |
| 6,718,571 B2 * | 4/2004 | Bartels | 5/81.1 R |
| 6,782,571 B1 * | 8/2004 | Josephson et al. | 5/601 |
| 6,820,292 B2 * | 11/2004 | Heimbrock | 5/81.1 R |
| 6,854,140 B2 * | 2/2005 | Bartels et al. | 5/601 |
| 6,857,143 B2 * | 2/2005 | McNulty | 5/81.1 C |
| 6,898,809 B2 * | 5/2005 | Davis | 5/81.1 R |
| 6,928,672 B2 * | 8/2005 | Pastyr et al. | 5/81.1 HS |
| 7,032,261 B2 * | 4/2006 | Heimbrock | 5/81.1 HS |
| 2002/0165438 A1 | 11/2002 | Bartels et al. | 600/300 |
| 2002/0166168 A1* | 11/2002 | Weedling et al. | 5/81.1 R |
| 2002/0174485 A1* | 11/2002 | Bartels | 5/601 |
| 2003/0070226 A1* | 4/2003 | Heimbrock | 5/81.1 R |
| 2003/0159212 A1* | 8/2003 | Patrick et al. | 5/81.1 R |
| 2003/0226202 A1* | 12/2003 | McNulty | 5/81.1 HS |
| 2004/0143905 A1* | 7/2004 | Pastyr et al. | 5/601 |
| 2005/0028273 A1* | 2/2005 | Weedling et al. | 5/81.1 R |
| 2005/0034230 A1* | 2/2005 | Weedling et al. | 5/81.1 R |
| 2005/0060804 A1* | 3/2005 | Heinl et al. | 5/601 |
| 2005/0102749 A1* | 5/2005 | Heimbrock | 5/81.1 HS |
| 2006/0000016 A1* | 1/2006 | Weedling et al. | 5/81.1 HS |
| 2006/0191070 A1* | 8/2006 | Heimbrock | 5/81.1 R |
| 2006/0225202 A1* | 10/2006 | Stackley et al. | 5/81.1 C |
| 2006/0282946 A1* | 12/2006 | Meyer | 5/81.1 HS |

FOREIGN PATENT DOCUMENTS

| | | |
|---|---|---|
| DE | 199 01 482 A1 | 8/2000 |
| DE | 101 11 801 A1 | 2/2002 |
| GB | 2 381 516 A | 7/2003 |

* cited by examiner

SUPPORT DEVICE FOR A PATIENT

The present patent document claims the benefit of the filing date under 35 U.S.C. §119(e) of Provisional U.S. Patent Application Ser. No. 60/499,509, filed Sep. 2, 2003, which is hereby incorporated by reference. The present patent document also claims priority to German Application No. 103 40 552.6, filed Sep. 1, 2003, which is hereby incorporated by reference.

FIELD OF THE INVENTION

The invention relates, in general, to clinical patient tables or support systems, and more particularly, to a patient support device which can be connected to patient placement devices of medical examination or treatment equipment of various types.

BACKGROUND OF THE INVENTION

Patients can be examined or treated by means of various types of medical equipment. For example, image-providing equipment for computer tomography (CT), MRI tomography (MRI), positron emission tomography (PET) or X-ray methods is available for examinations. For such examinations or treatments, electron-ray, lithotripsy or radiation therapy equipment, or simple operating tables may be employed. A patient who is to be treated or examined by means of such equipment is placed onto the patient placement device. The patient placement device can be fixedly connected with the respective equipment and in general consists of a patient support tabletop and a patient support device, on which the patient can be positioned and moved into the equipment. The patient support tabletop may also be a cot, stretcher, or the like. The patient is placed on a different support device while being transported to the patient placement device of the equipment or away from it, which can be moved from one location to another, for example from one type of equipment to another, by means of a patient transporting device, a so-called gurney.

A transfer of a patient, who may possibly be severely injured, between the patient support devices of the ambulance and the examination or treatment equipment can be potentially very hard on the patient and painful. Moreover, the transfer of the patient also places the involved medical personnel under a large bodily stress. Finally, such patient transfer can require the assistance of several people and uses up additional work time.

In order to avoid the transfer of a patient from one patient supporting device to another, it is known from DE 101 11 801 to employ a system consisting of several different types of medical equipment, as well as a single patient support device, wherein the patient support device can be separated from the respective patient placement device and can be connected to every other patient placement device. A board or a support plate, for example, can be provided as the patient support device, via which the patient can be placed while being prone.

The free interchange of the patient support device with the various types of examination/treatment equipment demands that the patient support device and the equipment be appropriately constructed in various ways. However, this results in difficulties in connection with MRI tomography. In general, the manufacturing materials which are normally used for producing patient support devices are not suitable for usage in MRI examination equipment. Instead, these patient support devices are mainly produced and designed for use in connection with other equipment, for example for X-ray procedures, and are made of carbon fiber materials. They typically must have a substantially high degree of transparency to X-rays for use in X-ray procedures. Other specific materials are usually employed for use with MRI equipment than for nearly all other examination or treatment equipment. MRI compatible materials must be non-conducting and completely non-magnetic, but may not be transparent to X-rays. Further, it is customary to place special signal-recording coils on the patient support device for MRI tomography on which the patient is placed in the same way as on cushions. These coils remain on the device when the MRI device is disconnected from the patient support table and may lead to disruptive image interferences when the device is connected to the table of a different examination device.

Up to now, patient support devices, which are intended to be used with both MRI equipment and other examination or treatment equipment, had to be developed from highly specialized materials as well as in the form of highly specialized support device structures. For example, X-ray patient support devices must not have any structural parts which would create interference shadows at defined X-ray entry angles, for example. However, this patient support device structural limitation makes it difficult to flexibly and adaptively address other demands made on the patient support device, for example opportunities for securing body parts of the patient in place or for attaching medical accessories.

OBJECT AND SUMMARY

The present invention is defined by the appended claims. This description summarizes some aspects of the present embodiments and should not be used to limit the claims.

An object is to disclose a patient support device which can be used in connection with medical examination or treatment equipment of different types without having to be substantially modified, which are of simple construction and which do not require the development of highly special materials.

One aspect is a patient support device which can be connected with patient placement devices of different types of medical examination and treatment equipment or of ambulances and which has a rigidity which is less than a minimal rigidity at which the patient support device is self-supporting.

The aspect is based on the realization that the patient support device onto which a patient is to be placed does not have to fulfill the function of bearing the patient. Instead, the patient support device can be structurally configured such that the patient resting thereon can be shifted, for example. In other words, the requirement that the patient support device needs to be self-supporting can be waived. Doing without this mechanical requirement permits an increased flexibility in the design of the patient support device in respect to those non-mechanical demands which must be made on the material of the support, allowing use in connection with MRI equipment as well as with all further types of examination or treatment equipment. In this case, there are a sufficient number of materials available, which are compatible with X-ray, as well as with MRI equipment, i.e. they can be both transparent to X-rays and electrically non-conducting and non-magnetic. One such a material is fiberboard. The patient support device can in particular be made very thin. Because of its reduced thickness, such a support device can be placed on the patient support device of an existing patient placement device and can be used there without it being necessary for the latter to be restructured. For use in MRI tomography, the patient support device can be placed on the signal-recording coils of the MRI support device of the patient placement device of the MRI tomograph. Because of its reduced thickness, there is hardly any weakening of the MRI signals on account of the now slightly increased distance between the patient and the coil.

Thus, one advantage is that the patient support device, while having a particularly simple structure of the support device and simultaneously minimizing or even omitting the use of highly specialized materials, can be employed in connection with all types of examination or treatment equipment. This results in the opportunity of transporting a severely injured patient between most examination devices and to the operating table without having to move him from one examination device to the other. As such, the patient, while being placed on the support device, possibly secured with straps and, lying on it, can be moved from one type of equipment to the other with the aid of the gurney.

In an advantageous aspect, the patient support device can have rollers on its underside with which it can be placed on a patient placement device. The shifting of the patient support device can thus be made easier in the course of the change from the medical device, for example, to the gurney.

In another advantageous aspect, the underside of the patient support device facilitates a build-up of an air cushion. Shifting of the patient support device is accordingly made easier by the air cushion in a way similar to rollers.

In another advantageous aspect, the patient support device has connectors to make a releasable connection with the patient placement device of medical examination or treatment equipment, or a gurney. Basically, a patient has to be secured when medical equipment is used. This releasable connection can provide for the dependable and secure positioning of the patient in the equipment, on the one hand, and on the other hand, the safety of the patient is substantially increased by minimizing potential sliding off or around. Securing can be further assured when the patient is secured on the support device by means of straps, and the support device is fixedly connected with the patient placement device of the examination apparatus. By integrating them into the patient support device, the connector for connecting the patient support device with a medical device can be arranged particularly flush and without interfering edges or protrusions.

In a further advantageous aspect, the patient support device has handles which can improve its maneuverability while being shifted. Shifting is made substantially easier by the handles, which can also be arranged particularly flush and without interfering edges or protrusions by being integrated into the patient support device.

In a further advantageous aspect, the patient support device has connectors as well as handles, and the connectors can be activated by operating the handles. By integrating the actuation of the connectors into the handles, an actuating device which would have to be additionally provided can be omitted, and the number of interfering edges and protrusions is further reduced.

Illustrative and exemplary embodiments of the invention are described in further detail below with reference to and in conjunction with the figures.

DETAILED DESCRIPTION OF DRAWINGS AND PREFERRED EMBODIMENTS

Figure 1:
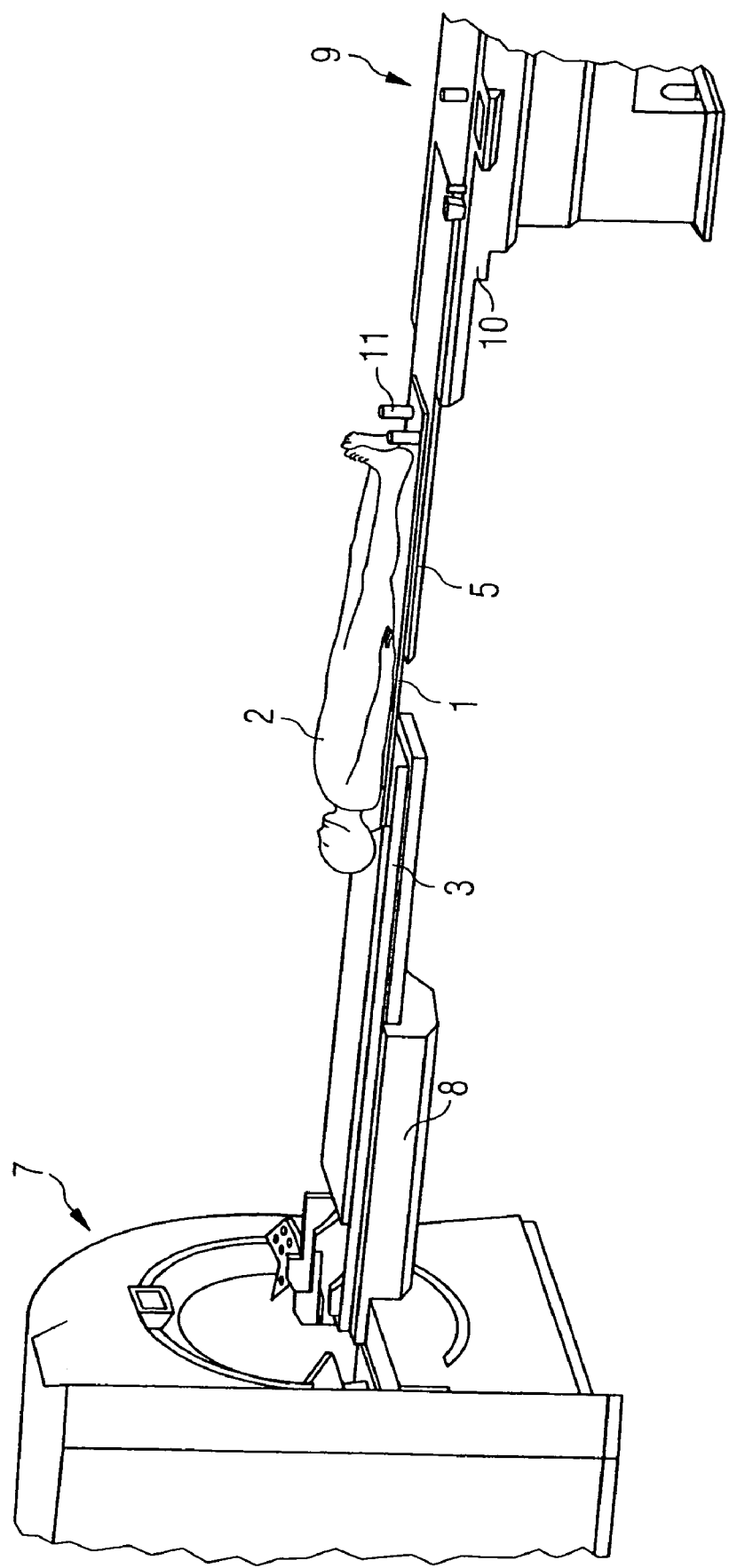
FIG. 1 illustrates schematically an embodiment of a patient support device, as well as MRI and X-ray equipment.

A system consisting of two pieces of medical equipment and a patient support device 1 is illustratively represented in FIG. 1. The two pieces of medical equipment are an MRI device 7 and an X-ray machine 9, partially represented in the area of the patient support device 1. A patient 2 rests on the patient support device 1 which can be pushed to one as well as to the other piece of equipment.

The MRI device 7 has a patient placement device 8, on which a patient to be examined is placed. An MRI patient support tabletop 3 is provided for this purpose, by means of which the patient is pushed into the MRI device 7. The patient support tabletop 3 is made of materials which are suitable for use in an MRI procedure. To be able to push the patient 2 into the MRI device 7, first the patient support device 1 is pushed onto the MRI patient support table 3. To make the pushing easier, the patient support device 1 has handles 11 arranged in its corners. The handles 11 are designed in such a way that they can be grasped by an operator for pushing or pulling the patient support device 1.

Once the patient support device 1 has been completely pushed onto the MRI patient support table 3, the latter can be pushed into the MRI device 7 or pulled out of it by means of a normal functioning of the patient placement device 8. The patient support device 1 remains in its position on the MRI patient support table 3 during the in and out movement relative to the MRI device 7.

If the patient 2 is not to be examined in the MRI device 7, but in the X-ray machine 9, the patient is pushed onto the X-ray patient support table 5 instead. The patient can be moved by means of the X-ray patient placement device 10 into or onto the X-ray machine 9.

Thin guide tracks or guide grooves can be installed on the X-ray patient support table 5, as well as on the MRI patient support table 3, for making the guidance and exact positioning of the patient support device 1 during shifting easier. Shifting of the patient support device 1 can be performed manually, as well as in a motor-driven or hydraulically driven manner.

The patient support device 1 can furthermore have arrangements, not represented, on which accessories which are to be shifted or transported together with the patient can be fastened. These accessories can be, for example, bottles of saline solution, devices for the continuous monitoring of EKG and blood pressure, or placement opportunities for long guide wires and catheters.

The patient support device 1 can consist of several segments, which are also not shown in the drawing FIGS. 1–6. These segments can offer adjustment options, for example for matching the patient support device to an operating table. These segments can moreover include a head portion which can be raised, so that the head of the patient 2 can be raised for the MRI examination, for example by means of a magnetic coil arranged thereon. Furthermore the patient support device 1 can have devices, also not represented, for fixing the head of the patient 2 in place and which can be solidly locked together with the operating board on a neurosurgical operating table, so that the head of the patient 2 is fixed in place, for example for trepanation. Further devices, not shown, for example straps, can be provided for fixing further parts of the body in place.

In the course of changing or moving from one type of medical equipment to the other, the patient 2 remains lying on the patient support device 1. Thus, repositioning the patient 1 between the two different examinations can be minimized, or even omitted. As such, the patient support device 1 may only need to be shifted instead of carrying it from one location to the other, which minimizes a self-supporting characteristic of the patient support device 1. Therefore, the material used to manufacture the patient support device 1 may not need to meet elaborate mechanical demands and instead can be selected such that it can be utilized without problems in an MRI procedure, as well as in an X-ray procedure. For example, it is possible to use radiation-resistant plastic materials, such as laminated paper like Pertinax.

Figure 2:
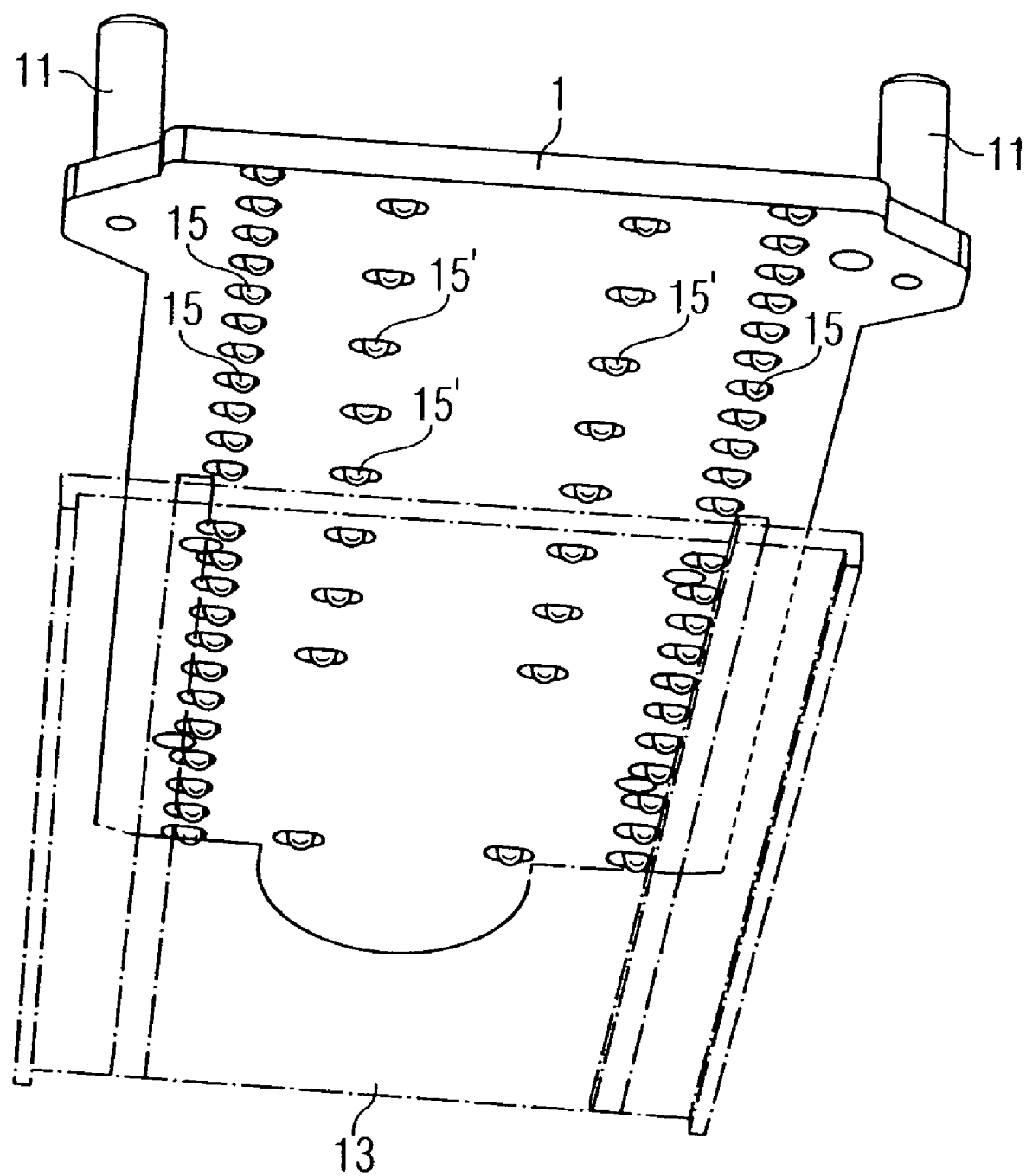
FIG. 2 is a bottom view of another embodiment of a patient support device with rollers.

The patient support device 1 with rollers 15, 15' is now represented in a bottom view in FIG. 2. This patient support device 1 partially rests on a patient support tabletop 13, indicated in dashed lines, which is a part of a piece of medical examination or treatment equipment, not represented. The patient support device 1 has handles 11, by means of which it can be easily shifted.

The rollers 15, 15' on the underside of the patient support device 1, with which the latter rests on the patient support table 13, are provided for reducing the mechanical resistance of the device against shifting. They are arranged such that a shifting of the patient support device 1 in the longitudinal direction is made easier. In one embodiment the rollers 15, 15' are seated in rolling bearings on the patient support device 1. In another embodiment, they are seated instead in roller bearings. Details of the seating of the rollers 15, 15' are not represented in the drawings.

In place of essentially cylindrical rollers, which make shifting of the patient support device 1 possible in only one direction, ball-shaped rollers are provided in a further embodiment, not represented. A greater part of a circumference of their ball shapes is embedded in the patient support device 1 and is seated there in such a way that they can be rotated in all directions. The remaining portion of the surface of the ball shape protrudes out of the underside of the patient support 1 and rests on the patient support tabletop 13. Like a track ball of a computer, the protruding portion of the surface of the ball shape can be rolled in every direction and as such reduces the mechanical resistance when shifting the patient support device 1 in any arbitrary direction.

Figure 3:
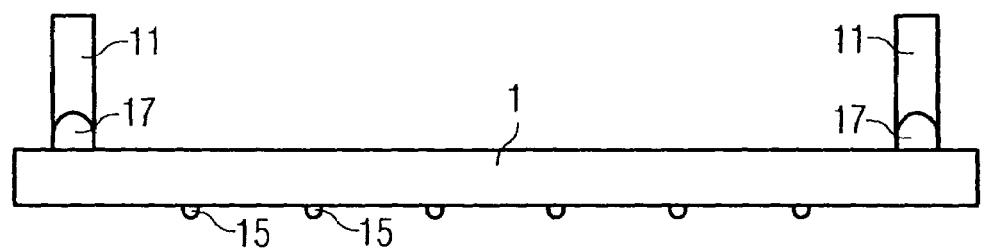
FIG. 3 is a lateral view of the patient support device with rollers illustrated in FIG. 2 with a connecting mechanism.

The patient support device 1 is represented in a lateral view in FIG. 3. The patient support device 1 has rollers 15, which are intended to make shifting easier. Handles 11 are provided, which can be grasped by an operator for shifting. The handles 11 are seated in a connecting mechanism 17. They are seated in the connecting mechanism 17 such that they can be used for shifting, on the one hand, and on the other hand can be operated for activating the connecting mechanism 17. The connecting mechanism 17 is constructed such that it can be activated by flipping the handles 11 over from a vertical position about a horizontal axis. By activating the connecting mechanism 17, connecting means 19, not shown or visible in FIG. 3, are activated, which enable the patient support device 1 to be connected to the patient support tabletop 13 of a piece of medical equipment. The connecting means 19 provide a releasable connection between the patient support tabletop 13 and the patient support device 1, which can be released again by operating or rotating the handles 11 in the opposite direction.

Figure 4:
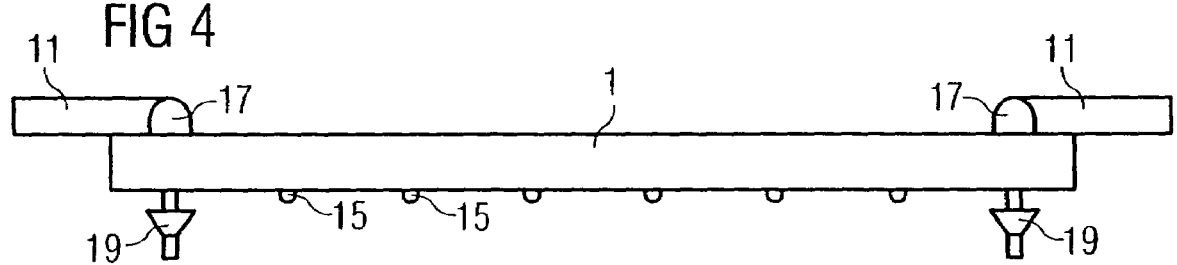
FIG. 4 is a lateral view of the patient support device illustrated in FIG. 3 with the connecting mechanism in an alternate position.

The patient support device 1 as in FIG. 3 is now represented in FIG. 4 with the connecting mechanism 17 activated. In this case, the connecting mechanism 17 was activated by flipping the handles 11 over; as such the connecting means 19 extend downward from the underside of the patient support device 1. In the embodiment of FIG. 4, the connecting means 19 are shown as bars or bolts, which can snap into associated counter-blocks of the non-represented patient support tabletop 13. Thus, a releasable connection between the patient support device 1 and the non-represented patient support tabletop 13 is made by activating the connecting mechanism 17. The connection can assure the stable positioning of the patient support device 1.

By flipping the handles 11 back into the previously described vertical position, the connecting means 19 are retracted back into the patient support device 1 and the connection is released.

Figure 5:
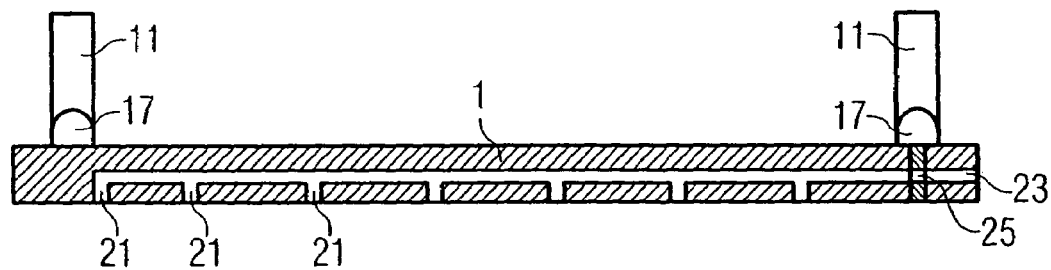
FIG. 5 is a lateral cross-sectional view of another embodiment of a patient support device provided with an air cushion.

A patient support device 1 with means for building up an air cushion is shown in a lateral cross-sectional view in FIG. 5. The lateral cross-sectional view represents a longitudinal cross-section through the patient support device 1. A conduit 23 extends inside the patient support device 1, which supplies nozzles 21 on the underside of the patient support device 1. The conduit 23 can be filled with ambient air under overpressure, for example compressed air, via an opening, shown at the right of FIG. 5. The compressed air can escape through the nozzles 21 at the underside of the patient support device 1 and there forms an air cushion between the latter and a patient support tabletop 13, not represented in the drawing figure, which is arranged underneath it. The air cushion makes shifting the patient support device 1 in any direction easier.

The patient support device 1 can furthermore have handles 11, via which it can be shifted, on the one hand, and wherein on the other hand a connecting mechanism 17 can be activated. The coupling or connecting mechanism 17 includes connector 19 with which the patient support device 1 can be connected to a patient support tabletop 13 located underneath it. In turn, the connector 19 can have a valve opening 25, through which the conduit 23 can be filled with compressed air. The valve opening 25 is arranged at the connector 19 in such a way that it opens the conduit 23 when the connecting mechanism 17 has not been activated, which can be seen in FIG. 6.

Figure 6:
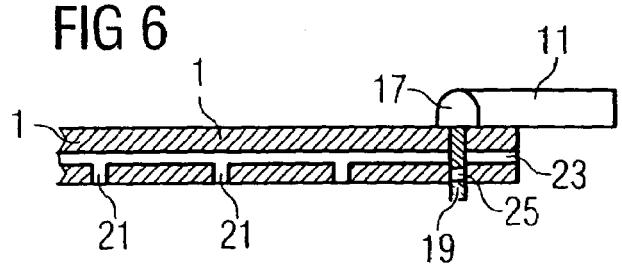
FIG. 6 is a lateral cross-sectional view of the patient support device of FIG. 5 with the air cushion deactivated.

The patient support device 1 as in the previous drawing figure is represented in FIG. 6, but with the connecting mechanism 17 activated. Activation of the connecting mechanism 17 takes place by flipping the handles 11 over from a substantially vertical position to a substantially horizontal position, so that the connector 19 extends out of the underside of the patient support device 1. In the course of being extended, it can engage a counter-block, not represented, of a patient support tabletop 13.

Along with the extension of the connector 19, the valve opening 25 provided therein can also be shifted along a vertical direction Shifting blocks or obstructs the conduit 23 and the nozzles 21 are no longer supplied with compressed air. As a result, no air cushion is built up on the underside of the patient support device 1. Once the patient support device 1 is connected with a patient support tabletop 13 via an activation of the connecting mechanism 17, the patient support device 1 can no longer be shifted and the air cushion is no longer needed. As such, the compressed air is turned off simultaneously with the connecting operation.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

What is claimed is:

1. A patient support device that supports a patient during medical examination and/or treatment comprises:
   a surface for placement of a patient;
   a material having a structural rigidity that is less than a minimal rigidity that enables the patient support device to be self-supporting while the patient is resting thereon;
   an underside having a configuration that enables the patient support device to be placed on a patient placement device; wherein the underside comprises rollers; and
   a connecting mechanism configured to connect the patient support device to the patient placement device, wherein the patient support device is connectable to the patient placement device.

2. The patient support device in accordance with claim 1, wherein the patient support device is releasably lockable to the patient placement device.

3. The patient support device in accordance with claim 1, further comprising at least one handle extending from the surface.

4. The patient support device in accordance with claim 3,
   wherein the connecting mechanism is activated by operating the at least one handle.

5. The patient support device in accordance with claim 3, further comprising securing elements to fixedly position parts of the body of the patient resting on the patient support device.

6. The patient support device in accordance with claim 1, further comprising one handle in proximity of each corner of the patient support device.

7. The patient support device in accordance with claim 1, further comprising securing elements to fixedly position parts of the body of the patient resting on the patient support device.

* * * * *